United States Patent
Rosa et al.

(10) Patent No.: US 9,549,915 B2
(45) Date of Patent: Jan. 24, 2017

(54) UREA COMPOUNDS AND THEIR USE AS ENZYME INHIBITORS

(71) Applicant: BIAL-PORTELA & CA, S.A., S. Mamede Do Coronado (PT)

(72) Inventors: Carla Patricia da Costa Pereira Rosa, S. Mamede Do Coronado (PT); Rita Gusmao De Noronha, S. Mamede Do Coronado (PT); Laszlo Erno Kiss, S. Mamede Do Coronado (PT); Patricio Manuel Vieira Araujo Soares Da Silva, S. Mamede Do Coronado (PT); Domenico Russo, S. Mamede Do Coronado (PT); Jorge Bruno Reis Wahnon, S. Mamede Do Coronado (PT); William Maton, S. Mamede Do Coronado (PT)

(73) Assignee: BIAL-PORTELA & CA, S.A., S. Mamede Do Coronado (PT)

( * ) Notice: Subject to any disclaimer, the term of this patent is extended or adjusted under 35 U.S.C. 154(b) by 0 days.

(21) Appl. No.: 14/416,675

(22) PCT Filed: Jul. 24, 2013

(86) PCT No.: PCT/PT2013/000048
§ 371 (c)(1),
(2) Date: Jan. 23, 2015

(87) PCT Pub. No.: WO2014/017936
PCT Pub. Date: Jan. 30, 2014

(65) Prior Publication Data
US 2015/0174103 A1   Jun. 25, 2015

Related U.S. Application Data

(60) Provisional application No. 61/674,970, filed on Jul. 24, 2012.

(51) Int. Cl.
*C07D 233/61* (2006.01)
*C07D 233/88* (2006.01)
(Continued)

(52) U.S. Cl.
CPC ........... *A61K 31/4164* (2013.01); *A61K 45/06* (2013.01); *C07C 209/00* (2013.01); *C07C 209/26* (2013.01);
(Continued)

(58) Field of Classification Search
CPC  A61K 31/4164; A61K 45/06; C07D 207/335; C07D 233/61; C07D 233/88; C07C 209/26; C07C 209/00
See application file for complete search history.

(56) References Cited

U.S. PATENT DOCUMENTS

| 4,051,252 A | 9/1977 | Mayer et al. |
| 4,331,678 A | 5/1982 | De'Ath et al. |

(Continued)

FOREIGN PATENT DOCUMENTS

| WO | 2005073199 A1 | 8/2005 |
| WO | 2010074588 A2 | 7/2010 |

(Continued)

OTHER PUBLICATIONS

Russo et al., U.S. Appl. No. 14/417,354, Preliminary Amendment filed May 21, 2015.
(Continued)

*Primary Examiner* — Joseph Kosack
*Assistant Examiner* — Amanda L Aguirre
(74) *Attorney, Agent, or Firm* — Banner & Witcoff, Ltd.

(57) ABSTRACT

A compound having the following structure:

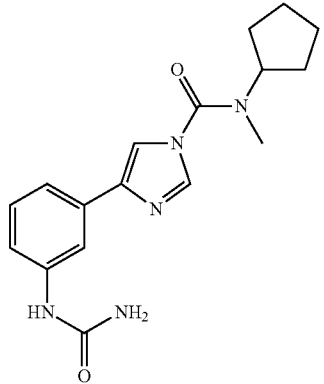

Formula A or a pharmaceutically acceptable salt or derivative thereof. The compound may be used in the treatment or prevention of a disorder selected from appetite regulation, obesity, metabolic disorders, cachexia, anorexia, pain, inflammation, neurotoxicity, neurotrauma, stroke, multiple sclerosis, spinal cord injury, Parkinson's disease, levodopa-induced dyskinesia, Huntington's disease, Gilles de la Tourette's syndrome, tardive dyskinesia, dystonia, amyotrophic lateral sclerosis, Alzheimer's disease, epilepsy, schizophrenia, anxiety, depression, insomnia, nausea, emesis, alcohol disorders, drug addictions such as opiates, nicotine, cocaine, alcohol and psychostimulants, hypertension, circulatory shock, myocardial reperfusion injury, atherosclerosis, asthma, glaucoma, retinopathy, cancer, inflammatory bowel disease, acute and chronic liver disease such as hepatitis and liver cirrhosis, arthritis and osteoporosis.

5 Claims, No Drawings

(51) Int. Cl.
*A61K 31/4178* (2006.01)
*A61P 31/00* (2006.01)
*A61K 31/4164* (2006.01)
*C07C 209/00* (2006.01)
*C07C 209/26* (2006.01)
*A61K 45/06* (2006.01)
*C07D 207/335* (2006.01)
*C07C 209/48* (2006.01)

(52) U.S. Cl.
CPC ......... *C07D 207/335* (2013.01); *C07D 233/61* (2013.01); *C07D 233/88* (2013.01)

(56) References Cited

U.S. PATENT DOCUMENTS

| | | | |
|---|---|---|---|
| 4,973,588 A | 11/1990 | Kihara et al. | |
| 5,578,627 A | 11/1996 | Takeda et al. | |
| 8,324,241 B2 * | 12/2012 | Huang | C07D 471/04 514/248 |
| 2005/0197348 A1 | 9/2005 | Zoller et al. | |
| 2009/0215824 A1 | 8/2009 | Zoller et al. | |
| 2012/0065191 A1 * | 3/2012 | Kiss | C07D 231/12 514/217.09 |

FOREIGN PATENT DOCUMENTS

| | | | |
|---|---|---|---|
| WO | 2012015324 A1 | 2/2012 | |
| WO | WO 2012038904 A1 * | 3/2012 | ........... C07D 401/12 |
| WO | 2014017936 A2 | 1/2014 | |

OTHER PUBLICATIONS

Dorwald, "Side Reactions in Organic Synthesis," 2005, Wiley: VCH Weinheim Preface, pp. 1-15 & Chapter 8, pp. 279-308.
Non-Final Office Action for U.S. Appl. No. 14/417,354 dated Feb. 19, 2016, 15 pages.
International Search Report and Written Opinion for PCT/PT2013/000050 mailed Jan. 30, 2014.
Heikki Kasnanen et al.: "3-Heterocycle-Phenyl N-Alkylcarbamates as FAAH Inhibitors: Design, Synthesis and 3D-QSAR Studies," Chemmedchem, vol. 5. No. 2., Feb. 1, 2010, pp. 213-231.
Da Silva R A et al.: "Zinc-promoted, iridium catalyzed reductive alkylation of primary amines with aliphatic ketones in aqueous medium," Tetrahedron Letters, vol. 51. No. 4, Jan. 27, 2010, pp. 689-691.
International Search Report for PCT/PT2013/000048 mailed Jul. 25, 2014.
Russo et al., U.S. Appl. No. 14/417,354, Restriction Requirement mailed Sep. 24, 2015.

* cited by examiner

UREA COMPOUNDS AND THEIR USE AS ENZYME INHIBITORS

FIELD OF THE INVENTION

The present invention relates to compounds and their uses, and in particular to compounds and their therapeutic use in the treatment or prevention of conditions having an association with substrates, such as the neurotransmitter anandamide, which are broken down by the fatty acid amide hydrolase (FAAH) enzyme.

BACKGROUND TO THE INVENTION

FAAH enzyme breaks down fatty acid amides such as anandamide (N-arachidonoylethanolamine), N-oleoylethanolamine, N-palmitoylethanolamine and oleamide. Anandamide, also known as N-arachidonoylethanolamine or AEA, is an endogenous cannabinoid neurotransmitter found in animal and human organs, especially in the brain. It has also been found that anandamide binds to the vanilloid receptor. Anandamide is degraded by the fatty acid amide hydrolase (FAAH) enzyme to ethanolamine and arachidonic acid. Accordingly, inhibitors of FAAH lead to elevated anandamide levels.

Anandamide is a neurotransmitter in the endocannabinoid system and stimulates the cannabinoid receptors. Cannabinoid receptors, such as CB1 and CB2, are G protein-coupled receptors. CB1 is found mainly in the central nervous system whereas CB2 is found mainly in peripheral tissue. The endocannabinoid system has been implicated in a growing number of physiological functions, both in the central and peripheral nervous systems and in peripheral organs. Modulation of the activity of the endocannabinoid system has been shown to have a potentially therapeutic effect on a wide range of disparate diseases and pathological conditions. Therefore, the endocannabinoid system, and the FAAH enzyme in particular, has become a therapeutic target for developing potential treatments for many diseases. The endocannabinoid system has been implicated in appetite regulation, obesity, metabolic disorders, cachexia, anorexia, pain, inflammation, neurotoxicity, neurotrauma, stroke, multiple sclerosis, spinal cord injury, Parkinson's disease, levodopa-induced dyskinesia, Huntington's disease, Gilles de la Tourette's syndrome, tardive dyskinesia, dystonia, amyotrophic lateral sclerosis, Alzheimer's disease, epilepsy, schizophrenia, anxiety, depression, insomnia, nausea, emesis, alcohol disorders, drug addictions such as opiates, nicotine, cocaine, alcohol and psychostimulants, hypertension, circulatory shock, myocardial reperfusion injury, atherosclerosis, asthma, glaucoma, retinopathy, cancer, inflammatory bowel disease, acute and chronic liver disease such as hepatitis and liver cirrhosis, arthritis and osteoporosis. The endocannabinoid system and the conditions with which it is associated is discussed in detail in Pacher et al. (2006) *Pharmacol. Rev.* 58:389-462.

In order to modulate the level of endogenous FAAH substrates, such as anandamide, which in turn modulate the endocannabinoid system, inhibitors of the FAAH enzyme have been developed. This allows conditions and diseases associated with the endocannabinoid system to be at least partially treated or prevented.

Since the substrates of FAAH bind to other receptors, e.g. the vanilloid receptor, and/or are involved in other signalling pathways, inhibitors of FAAH may also allow conditions or diseases associated with other pathways or systems, e.g. the vanilloid system, to be at least partially treated or prevented.

WO 2010/074588 discloses compounds which are inhibitors of FAAH. Käsnänen et al. (Heikki Käsnänen, Mikko J. Myllymäki, Anna Minkkilä, Antti O. Kataja, Susanna M. Saario, Tapio Nevalainen, Ari M. P. Koskinen, and Antti Poso. *Chem Med Chem* 2010, 5(2), 213-231) discloses carbamate compounds which are FAAH inhibitors. In particular, compound 6b is a FAAH inhibitor which contains an imidazole structure. However, this compound is a weak FAAH inhibitor compared to many of the other carbamate compounds described in this paper and which do not contain an imidazole structure.

SUMMARY OF THE INVENTION

In a first aspect, the present invention provides a compound having the following structure:

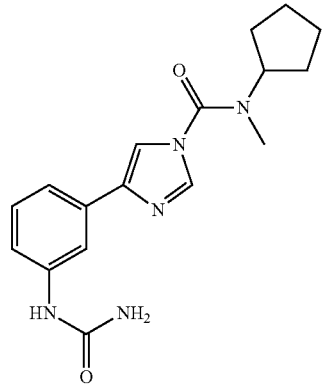

Formula A or a pharmaceutically acceptable salt or derivative thereof.

The compound of the invention has been found to modulate the activity of the enzyme fatty acid amide hydrolase (FAAH). Further, it has been shown to be relatively potent, to have relatively high peripheral selectivity (i.e. it inhibits FAAH to a greater extent in peripheral tissue compared to central nervous system tissue) and to be relatively metabolically stable. In particular, the compound of the invention has been shown to give better results relating to one or more of these properties compared to the compounds disclosed in WO 2010/074588.

'Pharmaceutically acceptable salts' of compounds of the present invention include salts with inorganic bases, salts with organic bases, salts with inorganic acids, salts with organic acids and salts with basic or acidic amino acids. Salts with acids may, in particular, be employed in some instances. Exemplary salts include hydrochloride salt, acetate salt, trifluoroacetate salt, methanesulfonate salt, 2-hydroxypropane-1,2,3-tricarboxylate salt, (2R,3R)-2,3-dihydroxysuccinate salt, phosphate salt, sulphate salt, benzoate salt, 2-hydroxy-benzoate salt, S-(+)-mandelate salt, S-(−)-malate salt, S-(−) pyroglutamate salt, pyruvate salt, p-toluenesulfonate salt, 1-R-(−)-camphorsulfonate salt, fumarate salt and oxalate salt. The compound of the present invention may be in either solvate (e.g. hydrate) or non-solvate (e.g. non-hydrate) form. When in a solvate form, additional solvents may be alcohols such as propan-2-ol.

'Pharmaceutically acceptable derivatives' of the compound of the invention are derivatives in which one or more groups of the compound is modified by reaction with another molecule. For example, derivatives include the modification of the $NH_2$ group to form $NHR$ or $NR_2$ in which R may be $C_{1-18}$ alkyl (e.g. $C_{1-6}$ alkyl), aryl, heteroaryl, $C_{3-8}$ cycloalkyl or combinations thereof. Such derivatives may be produced according to the following Scheme.

ties to the structure above. Suitable methods for testing these properties are well known to those skilled in the art and are described herein.

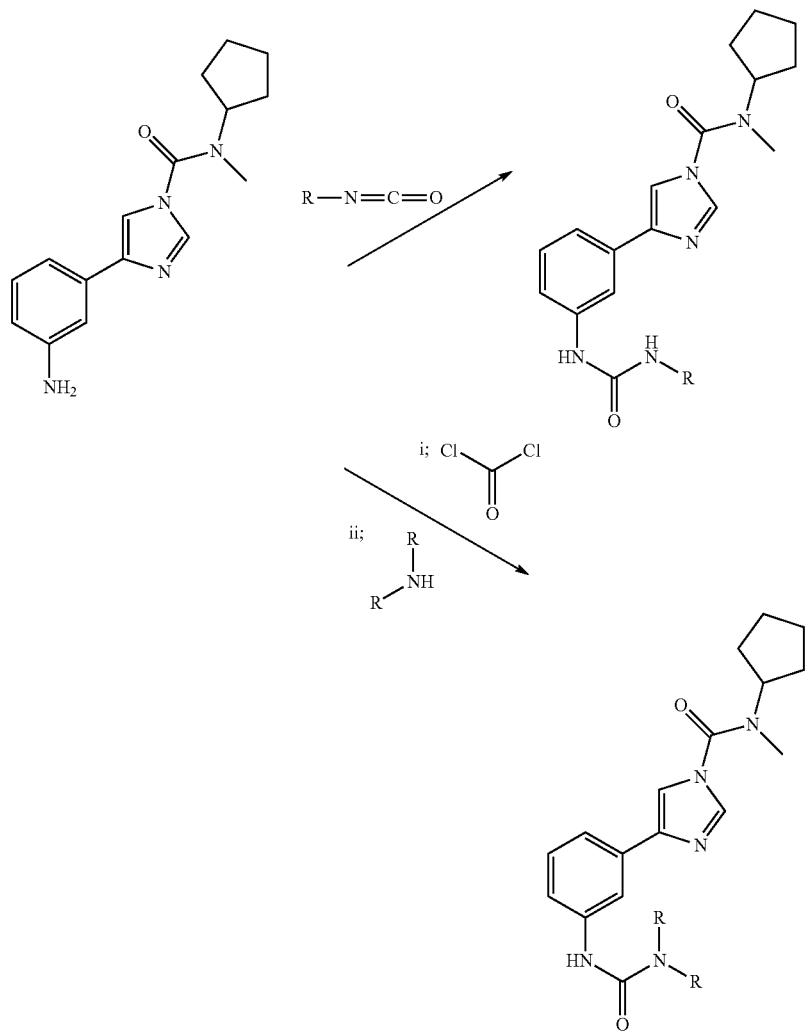

For example, derivatives include the products of reaction of the $NH_2$ group of 4-(3-aminophenyl)-N-cyclopentyl-N-methyl-1H-imidazole-1-carboxamide with R—N=C=O isocyanate (see R. G. Arnold, J. A. Nelson, J. J. Verbanc: Recent Advances in Isocyanate Chemistry *Chemical Reviews*, 57(1), 47-76, 1957 and the references therein) to form NH—(C=O)—NHR derivative, or with Cl—(C=O)—Cl and $NHR_2$ (see H. Babad, A. G. Zeiler: Chemistry of Phosgene *Chemical Reviews*, 73(1), 75-91, 1973 and the references therein) to form NH—(CO)—$NR_2$, in which R may be $C_{1-18}$ alkyl (e.g. $C_{1-6}$ alkyl), aryl, heteroaryl, $C_{3-8}$ cycloalkyl or combinations thereof. Pharmaceutically acceptable derivatives can be produced in any suitable way and methods for their production would be apparent to one skilled in the art based on well known principles in organic and medicinal chemistry (for example, suitable methods are disclosed in Vogel's Textbook of Practical Organic Chemistry, 5$^{th}$ edition, Longman, 1989). Obviously, the derivatives should be capable of inhibiting FAAH and should show peripheral selectivity, i.e. they should have similar proper- The term '$C_{x-y}$ alkyl' as used herein refers to a linear or branched saturated hydrocarbon group containing from x to y carbon atoms. For example, $C_{1-6}$ alkyl refers to a linear or branched saturated hydrocarbon group containing from 1 to 6 carbon atoms. Examples of $C_{1-6}$ alkyl groups include methyl, ethyl, n-propyl, isopropyl, n-butyl, isobutyl, sec-butyl, tert butyl, n-pentyl, isopentyl, neopentyl and hexyl. Preferably, the hydrocarbon group is linear.

The term 'aryl' as used herein refers to a $C_{6-12}$ monocyclic or bicyclic hydrocarbon ring wherein at least one ring is aromatic. Examples of such groups include phenyl, naphthalenyl and tetrahydronaphthalenyl.

The term 'heteroaryl' as used herein refers to a 5-6 membered monocyclic aromatic or a fused 8-10 membered bicyclic aromatic ring which monocyclic or bicyclic ring contains 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such bicyclic aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridyl, furopyridyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and imidazopyridyl.

The terms 'bicyclic ring' and 'fused' in the context of a bicyclic ring refers to two rings which are joined together across a bond between two atoms (e.g. naphthalene), across a sequence of atoms to form a bridge (e.g. quinuclidine) or together at a single atom to form a spiro compound (e.g. 1,4-dioxa-8-aza-spiro[4.5]decane and N,3,3-dimethyl-1,5-dioxaspirol[5.5]undecan-9-yl).

The term '$C_{x-y}$ cycloalkyl' as used herein refers to a saturated hydrocarbon ring of x to y carbon atoms which can be mono, bi or tricyclic. For example, $C_{3-8}$ cycloalkyl refers to a saturated mono, bi or tricyclic hydrocarbon ring of 3 to 8 carbon atoms. Examples of $C_{3-8}$ cycloalkyl groups include cyclopropyl, cyclobutyl, cyclopentyl, cyclohexyl, cycloheptyl and cyclooctyl.

General methods for the preparation of salts and derivatives are well known to the person skilled in the art. Pharmaceutical acceptability of salts and derivatives will depend on a variety of factors, including formulation processing characteristics and in vivo behaviour, and the skilled person would readily be able to assess such factors having regard to the present disclosure.

Where compounds of the invention may exist as alternative tautomeric forms (e.g. keto/enol, amide/imidic acid), the invention relates to the individual tautomers in isolation, and to mixtures of the tautomers in all proportions.

In accordance with a second aspect of the invention, there is provided a pharmaceutical composition comprising a compound according to the first aspect of the invention, together with one or more pharmaceutically acceptable excipients.

Pharmaceutical compositions of this invention comprise any of the compounds of the first aspect of the present invention with any pharmaceutically acceptable carrier, adjuvant or vehicle. Pharmaceutically acceptable carriers, adjuvants and vehicles that may be used in the pharmaceutical compositions of this invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, rectally, nasally, buccally, vaginally or via an implanted reservoir. Oral administration is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as that described in Ph. Helv, or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

The compounds of the present invention may be administered in a dose of around 1 to around 20,000 µg/kg per dose, for example, around 1 to around 10,000 µg/kg, around 1 to around 5,000 µg/kg, around 1 to around 3,000 µg/kg, around 1 to around 2,000 µg/kg, around 1 to around 1,500 µg/kg, around 1 to around 1,000 µg/kg, around 1 to around 500 µg/kg, around 1 to around 250 µg/kg, around 1 to around 100 µg/kg, around 1 to around 50 µg/kg or around 1 to around 25 µg/kg per dose depending on the condition to be treated or prevented, and the characteristics of the subject being administered with the compound. In many instances, the dose may be around 1 to around 10 μg/kg per dose. In particular embodiments, the dose may be around 250 μg/kg per dose, around 100 μg/kg, around 50 μg/kg or around 10 μg/kg per dose. The dosing regimen for a given compound could readily be determined by the skilled person having access to this disclosure.

In one particular embodiment, the pharmaceutical composition of the invention additionally comprises one or more additional active pharmaceutical ingredients. The compound of the invention may be administered with one or more additional active pharmaceutical ingredients, such as anandamide, oleoyl ethanolamide or palmitoyl ethanolamide. This may be in the form of a single composition comprising the compound of the invention and one or more additional active pharmaceutical ingredients. Alternatively, this may be in two or more separate compositions where the compound of the invention is contained in one composition and the one or more additional active pharmaceutical ingredients are contained in one or more separate compositions. Administration of the compounds of the present invention may therefore be simultaneous with, or staggered with respect to, the one or more additional active pharmaceutical ingredients.

In a third aspect, the present invention provides a compound according to the first aspect of the invention, or a composition according to the second aspect, for use in therapy.

In a fourth aspect, the invention provides a compound according to the first aspect of the invention, or a composition according to the second aspect, for use in the treatment or prevention of a condition whose development or symptoms are linked to a substrate of the FAAH enzyme.

The invention also provides the use of a compound according to the first aspect of the invention, or a composition according to the second aspect, in the manufacture of a medicament for the treatment or prevention of a condition whose development or symptoms are linked to a substrate of the FAAH enzyme.

A number of conditions whose development or symptoms are linked to a substrate of the FAAH enzyme are known to the skilled person. Some of these are discussed above.

In a fifth aspect, the invention also provides a method of treatment or prevention of a condition whose development or symptoms are linked to a substrate of the FAAH enzyme, the method comprising the administration, to a subject in need of such treatment or prevention, of a therapeutically effective amount of a compound according to the first aspect of the invention, or a composition according to the second aspect.

A compound according to the fourth aspect, or a method according to the fifth aspect, wherein the condition is a disorder associated with the endocannabinoid system.

In certain embodiments, the condition to be treated may be selected from:
(i) pain, in particular acute or chronic neurogenic pain such as migraine and neuropathic pain (for example diabetic neuropathic pain, post-herpetic neuralgia, trigeminal neuralgia); migraine; acute or chronic inflammatory pain, such as that associated with inflammatory diseases such as arthritis, rheumatoid arthritis, osteoarthritis, osteoporosis, spondylitis, gout, vasculitis, Crohn's disease, and irritable bowel syndrome; acute or chronic peripheral pain; cancer pain;
(ii) dizziness, vomiting, and nausea, in particular resulting from chemotherapy;
(iii) eating disorders, in particular appetite disorders, metabolic disorders, anorexia and cachexia of various natures;
(iv) neurological and psychiatric pathologies such as tremors, dyskinesias, dystonias, nausea, emesis, addictive disorders (such as addiction to a drug(s) or alcohol), spasticity, obsessive-compulsive behaviour, Tourette's syndrome, all forms of depression and anxiety of any nature and origin, insomnia, mood disorders, and psychoses such as schizophrenia;
(v) acute and chronic neurodegenerative diseases such as Parkinson's disease, Alzheimer's disease, senile dementia, Huntington's chorea, lesions related to cerebral ischaemia and to cranial and medullary trauma;
(vi) epilepsy;
(vii) sleep disorders, including sleep apnoea;
(viii) cardiovascular diseases such as heart failure, hypertension, circulatory shock, myocardial reperfusion injury, cardiac arrhythmias, arteriosclerosis/atherosclerosis, heart attack, cardiac ischaemia, vasculitis and renal ischaemia;
(ix) cancers, for example benign skin tumours, brain tumours and papillomas, prostate tumours, and cerebral tumours (glioblastomas, medulloepitheliomas, medulloblastomas, neuroblastomas, tumours of embryonic origin, astrocytomas, astroblastomas, ependymomas, oligodendrogliomas, plexus tumour, neuroepitheliomas, epiphyseal tumour, ependymoblastomas, malignant meningiomas, sarcomatosis, malignant melanomas, and schwannomas);
(x) disorders of the immune system, in particular autoimmune diseases, such as psoriasis, lupus erythematosus, diseases of the connective tissue or collagen diseases, Sjögren's syndrome, ankylosing spondylitis, undifferentiated spondylitis, Behcet's disease, autoimmune haemolytic anaemia, multiple sclerosis, amylotrophic lateral sclerosis, amyloidosis, graft rejection, diseases affecting the plasmacytic line, allergic diseases; immediate or delayed hypersensitivity, allergic rhinitis or conjunctivitis, contact dermatitis;
(xi) parasitic, viral or bacterial infectious diseases such as AIDS, and meningitis;
(xii) inflammatory diseases, in particular joint diseases such as arthritis, rheumatoid arthritis, osteoarthritis, spondylitis, gout, vasculitis, Crohn's disease, irritable/inflammatory bowel syndrome, asthma;
(xiii) osteoporosis;
(xiv) eye conditions such as ocular hypertension, retinopathy and glaucoma;
(xv) pulmonary conditions including diseases of the respiratory tracts, bronchospasm, coughing, asthma, chronic bronchitis, chronic obstruction of the respiratory tract, and emphysema;
(xvi) gastrointestinal diseases such as irritable/inflammatory bowel syndrome, inflammatory intestinal disorders, ulcers, diarrhea, urinary incontinence and bladder inflammation;
(xvii) acute and chronic liver diseases such as hepatitis and cirrhosis;
(xviii) neurological disorders such as neurotrauma, stroke, multiple sclerosis, spinal cord injury, Parkinson's disease, levodopa-induced diskinesia, Huntington's disease/chorea, Gilles de la Tourette, tardive diskinesia, dystonia, amytrophic lateral sclerosis, Alzheimer's disease, and epilepsy.

In a sixth aspect of the invention, there is provided a process for the synthesis of an acid salt of N-methylcyclopentylamine, the process comprising the reaction of cyclopentylamine with a chloroformate or di-tert-butyl carbonate, so as to form a cyclopentylcarbamate, followed by reduction of the cyclopentylcarbamate and acidification to the acid salt of N-methylcyclopentylamine.

The process of the sixth aspect can be used to efficiently produce an acid salt of N-methylcyclopentylamine, a key intermediate in the preparation of the compound of Formula A. The present process provides high yield and good quality product. A preferred acid salt is the HCl salt. However, other inorganic and organic acid salts are also feasible.

In embodiments, the cyclopentylcarbamate formation is conducted in basic conditions, for example, inorganic bases such as NaOH (e.g. 3M), NaHCO₃, Na₂CO₃ or K₂CO₃ or organic base such as triethyl amine, di-isopropyl ethyl amine, in an organic solvent such as THF, methyl THF, dioxane, methyl tert-butyl ether, or dichloromethane. The chloroformate used for this step may, for example, be $C_{1-4}$, such as ethyl, chloroformate. The reduction step may be conducted using lithium aluminium hydride (LAH), in an organic solvent such as THF or methyl THF. The temperature range is from 30° C. to reflux, preferably at 60° C. For isolation of the product, it is convenient to add an inorganic acid such as HCl, HBr, HI (e.g. concentrated) or an organic acid such as acetic acid, so as to form the corresponding acid salt of N-methylcyclopentylamine.

In a seventh aspect, the invention also provides a process for the synthesis of an acid salt of N-methylcyclopentylamine, the process comprising the reductive amination of cyclopentanone in the presence of an acid salt of methylamine.

In embodiments of the seventh aspect, the reduction takes place in the presence of a catalytic amount of precious metal supported on carbon, such as Pd/C (e.g. 5% or 10%), for example in the presence of an organic base such as triethylamine or di-isopropyl ethyl amine, and an alcohol-type solvent such as methanol, ethanol, propanol or butanol, under hydrogen. The pressure can vary from atmospheric pressure to 10 bar. A temperature of around 50-80 (or 60-70° C. may be used. A preferred acid salt in the seventh aspect is the HCl salt, wherein methylamine HCl is used in the process. However, other inorganic and organic acid salts are also feasible. Thus, inorganic acid salts such as HBr, HI, or an organic acid salt such as acetic acid, may be prepared by analogous methods.

The N-methylcyclopentylamine salt (such as HCl salt) produced according to the sixth or seventh aspects may subsequently be used for the preparation of a compound of Formula A, using any of the processes for preparation of that compound described herein. The invention thus also provides a process for the preparation of a compound of Formula A, in which a process according to the sixth or seventh aspects is comprised. Also provided is a compound of Formula A, obtained or obtainable by such a process.

DETAILED DESCRIPTION OF THE INVENTION

The invention will now be described in more detail by way of example only:
1. Synthetic Methodologies The methods used for synthesis of the compounds of the invention are illustrated by the general schemes below. All compounds and intermediates were characterised by nuclear magnetic resonance (NMR). The starting materials and reagents used in preparing these compounds are available from commercial suppliers or can be prepared by methods obvious to those skilled in the art. These general schemes are merely illustrative of methods by which the compounds of this invention can be synthesised, and various modifications to these schemes can be made and will be suggested to one skilled in the art having referred to this disclosure.

Room temperature in the following schemes means the temperature ranging from 20° C. to 25° C.

General Scheme for synthesis of N-cyclopentyl-N-methyl-4-(3-ureidophenyl)-1H-imidazole-1-carboxamide (Compound 1)

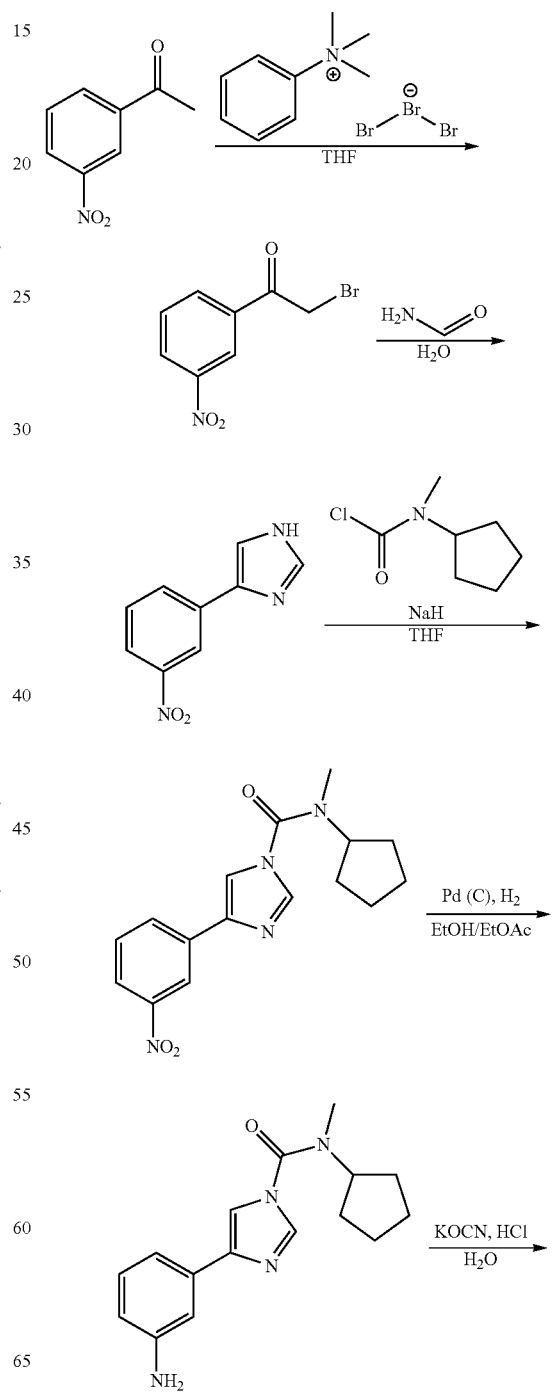

-continued

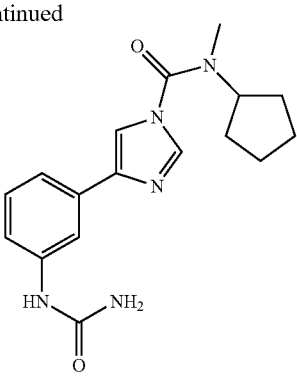

2-Bromo-1-(3-nitrophenyl)ethanone

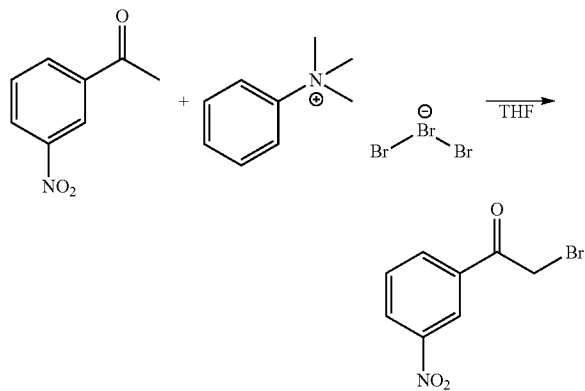

A solution of phenyltrimethylammonium tribromide (50.1 g, 133 mmol) in THF (200 mL) was added dropwise to a stirred solution of 1-(3-nitrophenyl)ethanone (20 g, 121 mmol) in THF (200 mL) at room temperature. The reaction mixture was allowed to stir at room temperature for 1 h. The white suspension was filtered and the filter cake was washed with THF, the filtrate was evaporated in vacuum to give a yellow oil. The residue was then dissolved in EtOAc and was washed with water. The organic layer was dried (MgSO$_4$) and evaporated in vacuum to give a yellow oil that solidified into an yellow solid. Solid recrystallised from propan-2-ol and final product was isolated as an off-white solid. 2-Bromo-1-(3-nitrophenyl)ethanone (20.5 g, 70% yield).

($^1$H, 600 MHz, 20° C., CDCl$_3$) δ: 8.83 (1H, t, J=2 Hz), 8.49 (1H, ddd, J=1.0, 2.3, 8.2 Hz), 8.34 (1H, ddd, J=1.0, 1.7, 7.8 Hz), 7.75 (1H, t, J=8.1 Hz), 4.49 (2H, s).

($^{13}$C, 150 MHz, 20° C., CDCl$_3$) δ: 189.3, 148.5, 135.1, 134.4, 130.2, 128.1, 123.8, 29.9 Melting point (mp): 90-91° C.

An alternative route for the bromination reaction is as follows:

To a solution of 3-Nitroacetophenone (1 wt, 1 eq) in Acetic acid (10 vol) is charged over a period of not less than 2 hours, maintaining the temperature below 30° C., a solution of bromine (0.34 vol, 1.08 eq). After stirring for 1 hour at a temperature between 25° C. and 30° C., the reaction is checked for completeness. After reaction completeness cold water (12 vol) is charged, forming a white precipitate. The suspension is stirred for an additional hour at 15° C. and then filtered. The cake is washed with water (4.5 vol). The product is dried under vacuum at a temperature not more than 45° C. until loss on drying <1.0%. The isolated yield of the brominated product was around 66%. This alternative approach may lend itself better to scaling-up.

4-(3-Nitrophenyl)-1H-imidazole

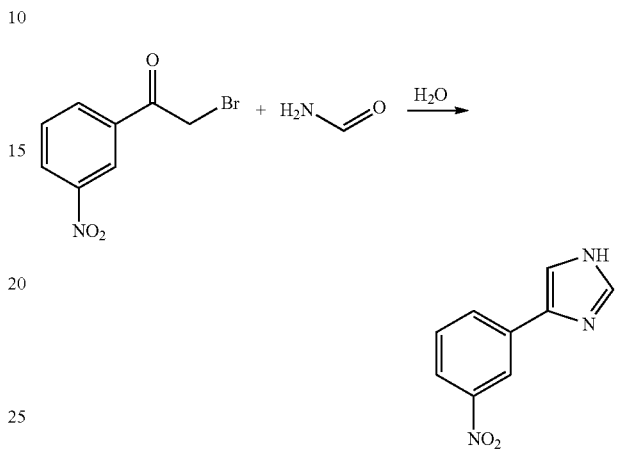

Water (8 mL) was added to a stirred suspension of 2-bromo-1-(3-nitrophenyl)ethanone (57.1 g, 234 mmol) and formamide (116 mL, 2.9 mol). The mixture was allowed to stir at 140° C. for 5 h. The brown residue was poured into 300 mL of water and the resulting precipitate was separated by filtration and was washed with a 1M HCl solution. The filtrate was basified with 50% NaOH and the resulting yellow precipitate was separated by filtration and was washed with water. The solid was dried and then recrystallised from propan-2-ol. 4-(3-Nitrophenyl)-1H-imidazole (7.05 g, 44% yield).

($^1$H, 600 MHz, 20° C., DMSO) δ: 12.37 (1H, s, br), 8.58 (1H, mt, J=2.0 Hz), 8.21 (1H, ddd, J=1.0, 1.6, 7.8 Hz), 8.02 (1H, ddd, J=1.0, 2.5, 8.2 Hz), 7.88 (1H, dd, J=1.2 Hz), 7.79 (1H, dd, J=1.1 Hz), 7.64 (1H, t, J=8.1 Hz)

($^{13}$C, 150 MHz, 20° C., DMSO) δ: 148.4, 137.9, 136.8, 136.6, 130.5, 130.0, 120.5, 118.3, 114.6

Melting point: 221° C. (dec.)

In terms of enhancements to this step of the process, it has been found that the use of formamide alone (i.e. without water) as suspension medium leads to increased yield, as does increasing the temperature from 140 to 170° C. (up to 80%). An enhanced protocol is thus as follows:

A solution of 2-bromo-1-(3-nitrophenyl)ethanone (1 wt, 1 eq) in Formamide (10 vol) is heated to 170° C. and stirred over a period of not more than 4 hours. After stirring for 4 hours the reaction is checked for completeness. After reaction completeness the mixture is cooled to r.t., and water (15 vol) is charged. The suspension is filtered and the cake is washed with 3N HCl (2 vol) and the mother liquor filtered again. Adjust the solution pH to 14 by addition of 50% NaOH (2 vol), maintaining the mixture temperature between 0° C. and 5° C. After stirring the suspension at 0/5° C. for NLT 30 minutes, filter and wash the cake with water (5 vol). The product is dried under vacuum at a temperature not more than 45° C. until loss on drying <1.0%.

Cyclopentyl(methyl)carbamic chloride

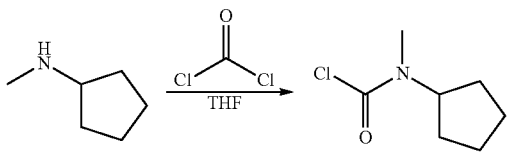

A solution of N-methylcyclopentanamine (10 g, 101 mmol) in THF (126 mL) was added dropwise to phosgene solution (63.7 mL, 121 mmol, 20% in toluene) at 0° C. to give a white suspension. The reaction mixture was allowed to stir at room temperature for 1 h. The solution was poured into ice. The organic layer was diluted with EtOAc, was separated washed with 1M HCl, dried (MgSO$_4$) and evaporated in vacuum to give a clear mobile oil. Cyclopentyl (methyl)carbamic chloride (13.1 g, 80% yield).

($^1$H, 600 MHz, 20° C., CDCl$_3$) δ: 4.65 (1H, m), 3.0, 2.93 (3H, 2 singlets), 1.92 (2H, m), 1.73 (2H, m), 1.59 (4H, m)

($^{13}$C, 150 MHz, 20° C., CDCl$_3$) δ: 149.7, 149.3, 61.1, 59.5, 33.1, 31.1, 28.8, 28.5, 24.0

The carbamoylation step can also be carried out using triphosgene/DCM and sodium carbonate, as follows:

A solution of Triphosgene (1.2 wt, 0.4 eq) in DCM (10 vol) is cooled to 0/5° C. and stirred over a period of not more than 10 minutes. A solution of N-Methylcyclopentylamine (1 wt, 1 eq) in DCM (5 vol) is charged maintaining the reaction temperature below 10° C. After the amine solution addition charge Na2CO3 (2.14 wt, 2 eq) and allow to warm to r.t. After stirring for 2 hours the reaction mixture is filtered and the cake is washed with DCM (1 vol). After concentration to dryness yellow oil is obtained and used as-is without further treatment.

N-Cyclopentyl-N-methyl-4-(3-nitrophenyl)-1H-imidazole-1-carboxamide

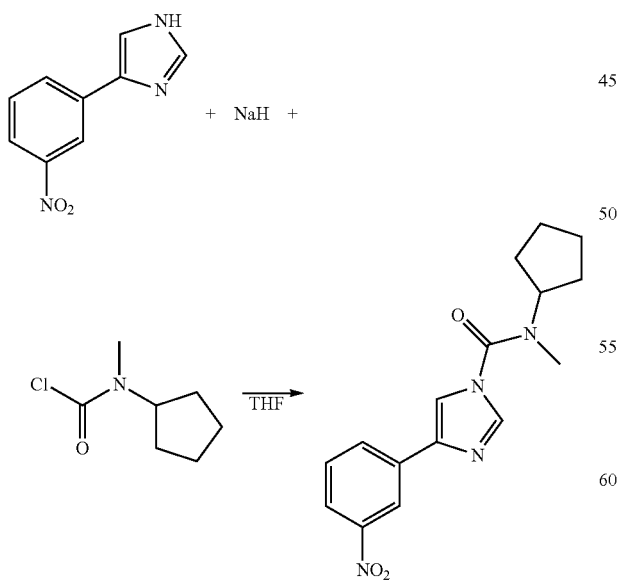

Sodium hydride (5.1 g, 127 mmol, 60% dispersion in mineral oil) was added portionwise to a stirred suspension of 4-(3-nitrophenyl)-1H-imidazole (20 g, 106 mmol) in THF (500 mL) at 0° C. The yellow suspension turned into a deep red suspension. The mixture was allowed to stir at room temperature for 30 minutes before adding a solution of cyclopentyl(methyl)carbamic chloride (25.6 g, 159 mmol) in THF (26 mL). The suspension was then allowed to stir at room temperature for 2 h. Water was added at 0° C. and the THF was evaporated. The organic residue was extracted with DCM, the organic layer was separated, dried (MgSO$_4$) and evaporated in vacuum to give a beige solid. The solid was triturated with propan-2-ol. N-Cyclopentyl-N-methyl-4-(3-nitrophenyl)-1H-imidazole-1-carboxamide (25.18 g, 76% yield).

($^1$H, 600 MHz, 20° C., CDCl3) δ: 8.63 (1H, mt, J=2.0 Hz), 8.16 (1H, ddd, J=1.0, 1.6, 7.8 Hz), 8.14 (1H, ddd, J=1.0, 2.3, 8.2 Hz), 7.96 (1H, d, J=1.3 Hz), 7.65 (1H, dd, J=1.3 Hz), 7.58 (1H, t, J=8.1 Hz), 4.45 (1H, m), 3.03 (3H, s), 1.98 (2H, m), 1.80 (2H, m), 1.73 (2H, m), 1.66 (2H, m)

($^{13}$C, 150 MHz, 20° C., CDCl3) δ: 151.3, 148.7, 140.1, 137.3, 134.9, 130.9, 129.7, 122.1, 119.9, 114.6, 59.4, 31.3, 28.9, 24.4

Melting point: 121-122° C.

4-(3-Aminophenyl)-N-cyclopentyl-N-methyl-1H-imidazole-1-carboxamide

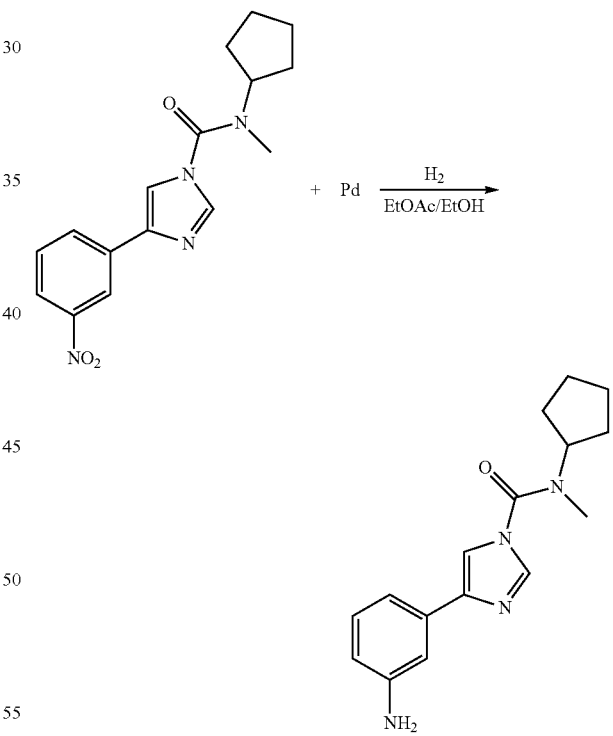

A mixture of Ethyl acetate (160 mL) and EtOH (160 mL) was added to wet Pd/C (0.846 g, 0.795 mmol, 10%) under an atmosphere of argon. To this was added N-cyclopentyl-N-methyl-4-(3-nitrophenyl)-1H-imidazole-1-carboxamide (5 g, 15.91 mmol) portionwise and the suspension was allowed to stir at room temperature overnight under an atmosphere of hydrogen. The mixture was flushed with argon and filtered through celite and the celite was washed with DCM. The filtrate was evaporated in vacuum to give a clear oil that solidified into a colourless solid. The solid was recrystallised from propan-2-ol. 4-(3-Aminophenyl)-N-cyclopentyl-N-methyl-1H-imidazole-1-carboxamide (3.62 g, 80% yield).

($^1$H, 600 MHz, 20° C., DMSO) δ: 8.06 (1H, d, J=1.3 Hz), 7.77 (1H, d, J=1.1 Hz), 7.08 (1H, t, J=1.9 Hz), 7.0 (1H, t, J=7.8 Hz), 6.98 (1H, md, J=7.7 Hz), 6.45 (1H, ddd, J=1.2, 2.3, 7.7 Hz), 5.07 (2H, s), 4.37 (1H, m), 2.92 (3H, s), 1.87 (2H, m), 1.68 (4H, m), 1.53 (2H, m)

($^{13}$C, 150 MHz, 20° C., DMSO) δ: 151.2, 148.8, 141.4, 137.3, 133.8, 129.0, 113.7, 112.9, 112.8, 110.4, 58.4, 31.2, 28.2, 24.0

Melting point: 108-109° C.

In an alternative embodiment, the aniline derivative product of this step can be used in the subsequent step without purification, i.e. such that this and the subsequent step can be telescoped.

N-Cyclopentyl-N-methyl-4-(3-ureidophenyl)-1H-imidazole-1-carboxamide (Compound 1)

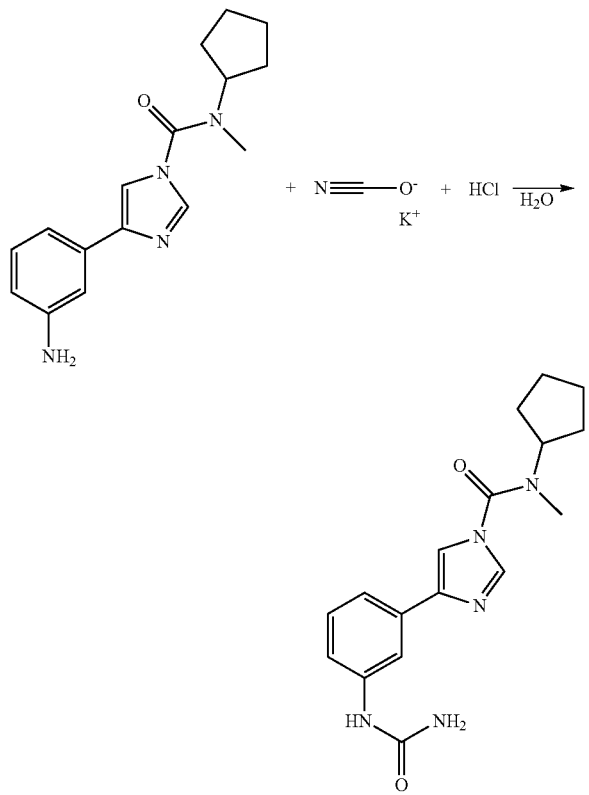

Potassium cyanate (0.445 g, 5.49 mmol) was added portionwise to a stirred solution of 4-(3-aminophenyl)-N-cyclopentyl-N-methyl-1H-imidazole-1-carboxamide (1.3 g, 4.57 mmol) in a mixture of 2N hydrogen chloride (2.286 mL, 4.57 mmol) in Water (4 mL) at 0° C. The mixture was allowed to stir at room temperature for 24 h. Potassium cyanate (0.220 g, 2.74 mmol) was added and the mixture was allowed to stir at room temperature for another night. Water was added and the organic layer was diluted with a mixture of DCM/propan-2-ol 7:3. The organic layer was separated and was washed with a 1N HCl aqueous solution. The organic layer was separated, dried (MgSO$_4$) and evaporated in vacuum to give a colourless foam. The product was purified by column chromatography (silica, DCM/MeOH 5%, 10%) and was isolated as a colourless solid. The solid was recrystallised from EtOH at 0° C. N-Cyclopentyl-N-methyl-4-(3-ureidophenyl)-1H-imidazole-1-carboxamide (0.403 g, 26% yield).

The compounds of the invention above were characterised by melting point and NMR as detailed below. NMR spectra were recorded on a Bruker 600 MHz Avance III spectrometer with solvent used as internal standard. 13C spectra were recorded at 150 MHz and 1H spectra were recorded at 600 MHz. Data are reported in the following order: approximate chemical shift (ppm), number of protons, multiplicity (br, broad; d, doublet; m, multiplet; s, singlet, t; triplet) and coupling constant (Hz).

Compound no. 1 (melting point: 204° C.).

($^{13}$C, 150 MHz, 20° C., DMSO) δ: 156, 151.1, 140.9, 140.8, 137.5, 133.7, 128.9, 117.9, 116.6, 114.2, 114.2, 58.4, 31.2, 28.2, 24.

($^1$H, 600 MHz, 20° C., DMSO) δ: 8.55 (1H, s), 8.09 (1H, d, J=1.2 Hz), 7.86 (1H, d, J=1.2 Hz), 7.85 (1H, t, J=1.8 Hz), 7.35 (1H, md), 7.34 (1H, md), 7.22 (1H, t, J=7.8 Hz), 5.84 (2H, s), 4.36 (1H, m), 2.93 (3H, s), 1.87 (2H, m), 1.69 (4H, m), 1.54 (2H, m).

An enhancement to this final step (urea formation on the phenyl ring) consists of using acetic acid as solvent for the 4-(3-aminophenyl)-N-cyclopentyl-N-methyl-1H-imidazole-1-carboxamide instead of water. This leads to an improvement in yield (around 78%), and an improved isolation protocol. The enhanced step may be described as follows: 4-(3-aminophenyl)-N-cyclopentyl-N-methyl-1H-imidazole-1-carboxamide is dissolved in AcOH (8.8 vol) at room temperature. To the resulting solution at room temperature is added a solution of potassium cyanate (0.65 wt, 2.5 eq) in water (0.9 vol). The resulting solution is stirred at room temperature until reaction completion (starting material<0.1%). Within 1 h, the precipitation of the urea product occurred. To the resulting slurry is added water (5 vol), and more solid crashes out. The beige suspension is then aged for 1 h at room temperature, and filtered. The beige solid is washed with water (10 vol), dried under vacuum oven until loss on drying <1.5%.

In case this enhanced step (using acetic acid) leads to an N-acetylated aniline impurity, a recrystallisation may be performed. This may be as follows:

To a solution of the urea product (1 wt) in acetic acid (5 vol) at room temperature was added drop wise water (5 vol) over 30 minutes. After having seeded, water (2 vol) was added and the slurry was aged at room temperature for 1 h. The slurry is cooled to 10° C., stirred at 10° C. for at least 1 h and filtered. The off white solid is washed with a 9:1 mixture of water/acetic acid (2 vol), water (10 vol), dried in a vacuum oven at 55° C. The off white solid (0.82 wt) is then dissolved in acetic acid (3.96 vol) at room temperature and water (4.1 vol) was added drop wise over 30 minutes. To the solution was then added seed, followed by water (1.6 vol). The resulting slurry was stirred at room temperature for at least 1 h and then cooled to 10° C. After aging the slurry at 10° C. for at least 1 h, the solid is filtered, washed with a 9:1 mixture of water/acetic acid (1.6 vol), water (10 vol), dried in a vacuum oven at 55° C. until loss on drying is <1.5%.

2. Biological Efficacy

In vivo testing was performed according to the protocol described below. BRh (brain homogenate) indicates inhibition in central nervous tissue, in this case, brain, and LVh (liver homogenate) indicates inhibition in peripheral tissue, in this case, liver. The controls were the reaction mix minus the test compounds. Therefore, a low value for the test compound indicates a strong inhibitor. A value of 100 indicates that no measurable inhibition took place.

In Vivo Protocol
Animal Treatment

The animals used for experiments were male NMRI mice (weighing 27-44 g) obtained from Interfauna Ibérica (Spain). Mice were kept 5 per cage, under controlled environmental conditions (12 hr light/dark cycle and room temperature 22±1° C.). Food and tap water were allowed ad libitum and the experiments were all carried out during daylight hours.

Animals were administered 30 mg/kg or 3 mg/kg compound of the invention or comparator compounds via oral route (8 ml/kg; compound suspended in 0.5% carboxymethylcellulose (CMC) or solubilized in water) or vehicle (controls) using animal feeding stainless steel curve needles (Perfectum, U.S.A.). Fifteen minutes before sacrifice animal were anesthetized with pentobarbital 60 mg/kg administered intraperitoneally. A fragment of liver, left lung lobe and brain without cerebellum were removed and put in plastic vials containing membrane buffer (3 mM $MgCl_2$, 1 mM EDTA, 50 mM Tris HCl pH 7.4). Tissues were stored at -30° C. until analysis.

Animals were always fasted overnight before administration of compounds except for time points of >18 h, where food was removed on the morning of day of administration and the compound was administered in the afternoon of the same day. Animals were then given water but nothing else.

All animal procedures were conducted in strict adherence to the European Directive for Protection of Vertebrate Animals Used for Experimental and Other Scientific Purposes (86/609CEE) and Portuguese legislation (Decreto-Lei 129/92, Portarias 1005/92 e 1131/97). The number of animals used was the minimum possible in compliance with current regulations and scientific integrity Reagents and Solutions Anandamide [ethanolamine-1-$^3$H-] (40-60 Ci/mmol) was obtained from American Radiochemicals. All other reagents were obtained from Sigma-Aldrich. Optiphase Supermix was obtained from Perkin Elmer and activated charcoal were obtained from Sigma-Aldrich.

Tissue Preparation

Tissues were thawed on ice and were homogenized in 10 volumes of membrane buffer (3 mM $MgCl_2$, 1 mM EDTA, 50 mM Tris HCl pH 7.4) with either Potter-Elvejhem (brains—8 strokes at 500 rpm) or Heidolph Diax (livers—2 strokes at position 5 for 20 sec with 30 sec pauses).

Total protein in tissues was determined with the BioRad Protein Assay (BioRad) using a standard curve of BSA (50-250 μg/ml).

Enzymatic Assay

Reaction mix (total volume of 200 μl) contained: 2 μM AEA (2 μM AEA+5 nM $^3$H-AEA), 0.1% fatty acid free BSA, 15 μg (brain), 5 μg (liver) or 50 μg (lung) protein, in 1 mM EDTA, 10 mM Tris pH 7.6. After a 15 min pre-incubation period at 37° C., reaction was started by the addition of the substrate solution (cold AEA+radiolabelled AEA+BSA). Reaction was carried out for 10 min (brain and lung) or 7 min (liver) before termination by the addition of 400 μl activated charcoal suspension (8 g charcoal in 32 ml 0.5 M HCl in continuous agitation). After a 30 min incubation period at room temperature with agitation, charcoal was sedimented by centrifugation in microfuge (10 min at 13000 rpm). 200 μl of the supernatant were added to 800 μl Optiphase Supermix scintillation cocktail previously distributed in 24-well plates. Counts per minute (cpm) were determined in a MicrobetaTriLux scintillation counter.

In each assay blanks (without protein) were prepared.

The percentage of remaining enzymatic activity was calculated with respect to controls and after blank subtraction.

$ED_{50}$ Determination

The test compounds were given in increasing doses (10, 3, 1, 0.3, 0.03 and 0.01 mg/kg) to the animals and at 8 h post-administration FAAH activity was determined according to the aforementioned in-vivo protocol, then $ED_{50}$ values were calculated by "Prisma" software with 95% of confidence intervals.

CYPs Metabolic Stability Assay

Stability of the test compounds was performed in MLM (mouse liver microsomes) or HLM (human liver microsomes) in the presence and in the absence of NADPH.

The stability was measured using the incubation mixture (100 μl total volume) contained 1 mg/ml total protein, $MgCl_2$ 5 mM and 50 mM K-phosphate buffer. Samples were incubated in the presence and in the absence of NADPH 1 mM. Reactions were pre-incubated 5 min and the reaction initiated with the compound under test (50Φ for HLM and 500Φ for MLM). Samples were incubated for 60 min in a shaking water bath at 37° C. The reaction was stopped by adding 100 μl of acetonitrile. Samples were then centrifuged, filtered and supernatant injected in HLPC-MSD. Test compounds were dissolved in DMSO and the final concentration of DMSO in the reaction was below 0.5% (v/v). At TO acetonitrile was added before adding the compound. All experiments were performed with samples in duplicate.

Compound 1 (N-cyclopentyl-N-methyl-4-(3-ureidophenyl)-1H-imidazole-1-carboxamide; also referred to as the compound of Formula A, above) was tested. Also, two comparator compounds were tested which are disclosed in WO 2010/074588. These are as follows:

Comparator compound 1-N-cyclohexyl-4-(3-guanidinophenyl)-N-methyl-1H-imidazole-1-carboxamide.

Comparator compound 2-N-cyclopentyl-4-(4-fluoro-3-hydroxyphenyl)-N-methyl-1H-imidazole-1-carboxamide.

Comparator compound 1 is structurally similar to compound 1, although there are clear differences between these compounds. Comparator compound 2 is also structurally similar to compound 1 but, again, there are clear differences between these two compounds.

|  | FAAH Activity (%) Br.h.3 mg/kg. 8 h.po | FAAH Activity (%) Lv.h.3 mg/kg. 8 h.po |
| --- | --- | --- |
| Compound 1 | 85.1 | 0.7 |
| Comparator Compound 1 | 86.2 | 20.3 |
| Comparator Compound 2 | 121.1 | 2.1 |

As can be seen from the above table, compound 1 is the most potent compound in terms of FAAH inhibition in the liver. In particular, compound 1 is much more potent than comparator compound 1.

Peripheral selectivity can be calculated by dividing the FAAH activity in the liver by the FAAH activity in the brain. When doing this, a lower number shows a compound is peripherally more selective. The results are given in the table below:

|  | Peripheral Selectivity |
| --- | --- |
| Compound 1 | 0.008 |
| Comparator Compound 1 | 0.235 |
| Comparator Compound 2 | 0.017 |

These results show that compound 1 is the most peripherally selective compound by more than a factor of 2. Further, compound 1 is much more peripherally selective than comparator compound 1.

Additional data relating to the activity of FAAH at various concentrations for compound 1 and comparator compound 2 are given in the table below:

| | FAAH Activity (%) mouse Liver | | | | |
|---|---|---|---|---|---|
| | 1 h | | 8 h | | |
| | 3 mg/kg | 10 mg/kg | 3 mg/kg | 1 mg/kg | 0.1 mg/kg |
| Compound 1 | 1.9 | 0.4 | 0.7 | 1.6 | 6.4 |
| Comparator Compound 2 | 17.0 | 1.2 | 2.1 | 4.9 | 73.8 |

As can be seen, at all doses, the FAAH activity is much lower following administration of compound 1 compared to comparator compound 2. In particular, at 0.1 mg/kg at 8 hours post-dose, the FAAH activity is significantly lower for compound 1 compared to comparator compound 2. This shows that compound 1 is significantly more potent than comparator compound 2. At 0.1 mg/kg, compound 1 is more than 10-fold more potent than comparator compound 2. This is a surprisingly big difference in potency. This data is also evidence that compound 1 is metabolically stable since, when conducting inhibition experiments in vivo, the metabolic stability of the compound will also play a role in the level of inhibition and the length of time over which inhibition takes place.

The table below shows FAAH inhibition $ED_{50}$ data (median effective dose, the dose of compound required to produce 50% inhibition of FAAH in liver) of the compounds after p.o. administration in mouse. Confidence intervals (95%) are included.

| Compound | Liver $ED_{50}$ (95CI) (mg/kg) | Time (h) |
|---|---|---|
| Compound 1 | 0.03 (0.02; 0.04) | 1 |
| Comparator Compound 2 | 0.17 (0.13; 0.23) | 8 |

The below table shows the metabolic stability of compound 1 and comparator compound 2. The stability data are given as % of remaining compound after 1 h exposure to MLM or HLM. 100% means no metabolic reaction at all and 0% corresponds to full enzymatic degradation. "CYP−" refers to the absence of cofactor (NADPH) which is essential for CYP metabolic reactions. Therefore "CYP−" can be regarded as control value. "CYP+" refers to the presence of cofactor and the enzymatic degradation may take place according to the stability of the test compound. As can be seen, compound 1 is more stable than comparator compound 2 in both MLM and HLM.

| | Metabolic Stability (% of Remaining) | | | |
|---|---|---|---|---|
| | Mouse | | Human | |
| | CYP+ | CYP− | CYP+ | CYP− |
| Compound 1 | 96 | 95 | 82 | 99 |
| Comparator Compound 2 | 53 | 92 | 70 | 92 |

3. Determination of $IC_{50}$ of Compound 1
3.1 Materials and Methods
a) Reagents and Solutions Anandamide [ethanolamine-1-$^3$H-] was obtained from American Radiochemicals—with a specific activity of 60 Ci/mmol. All other reagents were obtained from Sigma-Aldrich. Optiphase Supermix was obtained from Perkin Elmer and activated charcoal was obtained from Sigma.

b) Tissue Preparation

Frozen brains from 4 Wistar rats were homogenized in 20 ml 1 mM $MgCl_2$, 20 mM HEPES (4-(2-hydroxyethyl)-1-piperazineethanesulfonic acid) pH 7.0 with Potter-Elvejhem (8 strokes at 500 rpm). Homogenates were centrifuged for 20 min at 36000 g at 4° C. (Beckman, 70Ti rotor). Pellets were resuspended in 15 ml of the same buffer and centrifuged under the same conditions. Pellets were resuspended in 15 ml of the same buffer and incubated for 15 min at 37° C. after which they were centrifuged for 20 min at 36000 g at 4° C. Each pellet was then resuspended in 10 ml 3 mM $MgCl_2$, 1 mM EDTA (Ethylenediaminetetraacetic acid), 50 mM Tris (2-Amino-2-hydroxymethyl-propane-1,3-diol) pH 7.4 and protein determined with the BioRad Protein Assay (BioRad) using a standard curve of BSA (Bovine Serum Albumin) (50-250 μg/ml).

Membrane suspensions are aliquoted and stored at −30° C.

c) Enzymatic Assay

Reaction mix (total volume of 200 μl) contained: 2 μM AEA (2 μM AEA+5 nM $^3$H-AEA), 0.1% fatty acid free BSA, 5 or 10 μg protein, in 1 mM EDTA, 10 mM Tris pH 7.6 and compound 1 at various concentrations. Stock solution (10 mM) was prepared in 100% DMSO (dimethyl sulfoxide) and the DMSO concentration in the assay will be 0.1%. After a 15 min preincubation period at 37° C., reaction was started by the addition of the substrate solution (cold AEA+radiolabelled AEA+BSA). Reaction was carried out for 10 min before termination by the addition of 400 μl activated charcoal suspension (8 g charcoal in 32 ml 0.5 M HCl in continuous agitation). After a 30 min incubation period at room temperature with agitation, charcoal is sedimented by centrifugation in microfuge (10 min at 15000 g). 200 μl of the supernatant was added to 800 μl Optiphase Supermix scintillation cocktail previously distributed in 24-well plates. Counts per minute (CPM) or disintegrations per minute (DPM) were determined in a MicrobetaTriLux scintillation counter. In each assay blanks (no protein) and controls (no compound) were present.

d) Test Systems

Wallac 1450 MicrobetaTriLux scintillation counter.

e) Test Method

Counting conditions were the following:

| | |
|---|---|
| Labels: | H-3 |
| Cassette type: | 24 wells, 4 by 6 |
| Counting mode: | CPM or DPM |
| Sample type: | Normal |
| Paralux used: | No |
| Counting time: | 10 min |
| CPM norm.: | Norm_H3 (0) for CPM or 3H AEA standardization for DPM |
| Status: | n |
| Corrections | |
| BGND corr.: | Off |
| CLM corr.: | Off |
| Autoquench corr.: | No for CPM, NA for DPM |
| Counting control | |
| Precision: | 0.2 |
| Repeats: | 1 |
| Cycles: | 1 |
| Cycle delay: | 0 |
| Plate delay: | 0 |
| Plate orientation: | Normal |
| Detector setup: | Normal |
| Window 1: | 5-360 | f) Other Equipment

Spectramax Plus—SOFTmax® PRO Software version 3.0 g) Data Acquisition and Analysis

Raw data acquisition was performed with the software "Microbeta TriLux Windows workstation version 4.01".

Data analysis was performed using Prism 5 for Windows software, version 5.02 (GraphPad Software Inc., San Diego, Calif.). $IC_{50}$ value of compound 1 was determined by fitting experimental data to the log(inhibitor) vs normalized response—Variable slope equation:

$$Y = \frac{100}{1 + 10^{((LogIC50-X) \cdot HillSlope)}}$$

3.2 Results

Using this protocol, compound 1 was determined to have an $IC_{50}$ of 27 nM.

As can be seen from all the results above, compound 1 is significantly more potent, more peripherally selective and/or more metabolically stable than either of comparator compounds 1 and 2.

4. Synthesis of HCl Salt of N-Methylcyclopentylamine 4.1 Carbamate Reduction Method

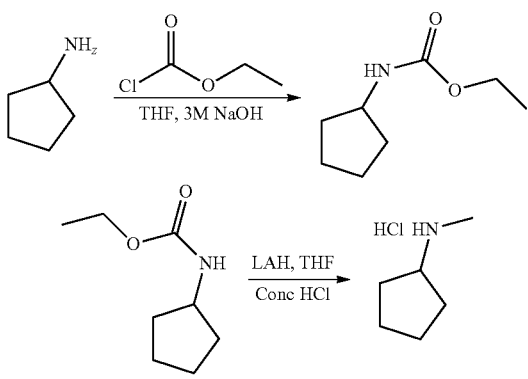

Step 1: Formation of Ethyl Carbamate

To a solution of cyclopentylamine (3 ml, 30.3 mmol) in THF (20 mL) at 0° C. were added respectively 3M sodium hydroxide (15.15 ml, 45.5 mmol) and ethyl chloroformate (3.47 ml, 36.4 mmol). The resulting biphasic mixture was stirred for 4 h at room temperature. The reaction mixture was diluted with MTBE (30 mL) and ammonium hydroxide (5 mL). The resulting mixture was stirred at room temperature for 10 minutes and then allowed to separate. The organic layer was washed with water, 0.5M HCl, dried over $Na_2SO_4$, filtered. The filtrate was concentrated under reduced pressure. Ethyl cyclopentylcarbamate (4.35 g) was obtained as colorless oil in 95% yield and was used in the next step without further purification This reaction proceeds very well. The yield and the quality of the product were high.

Step 2: Reduction of Ethyl Carbamate

The reduction of carbamates to the corresponding methyl amine is well known in general. This reduction requires usually the use of an excess of lithium aluminum hydride (LAH) in THF at reflux. However, the use of lithium aluminum hydride in large scale may require a more complex work up. Therefore, the Fieser work-up was used (for x g of LAH, use x ml of water, x mL of 15 to 25% NaOH then followed by 3x ml, of water) which is safer and easier to handle. A first attempt was successfully performed on the t-Butyl carbamate using LAH, Fieser work up followed by formation of the hydrochloride salt resulting from the addition of concentrated HCl. The N-methyl cyclopentylamine hydrochloride was obtained in 63% after isolation. The quality and the yield resulting from this first attempt led to a repeat using the ethyl carbamate, which led to a Molar yield of 83%, and a Quality range: >98% by NMR.

To a suspension of LAH (2,414 g, 63.6 mmol, 5 eq) in THF (20 mL) at room temperature under nitrogen was added a solution of ethyl cyclopentyl carbamate (2 g, 12.72 mmol) in THF (8 mL) over 20 minutes. Note: gas evolution. The dropping funnel was rinsed with THF (2 mL). The reaction mixture was heated to 65° C. (internal temperature, reflux) during 6 h. The suspension was cooled to 0° C. (water-ice bath). The suspension was diluted with MTBE (30 mL). To the suspension were added dropwise 2.4 mL of water (strong gas evolution and exothermic reaction was observed), dropwise 3.6 mL of 10% NaOH (good stirring is necessary) and finally dropwise 7.2 mL of water. The resulting slurry was warmed to room temperature and stirred for 30 minutes at room temperature. To the white suspension was added MgSO4 (10 g). The resulting slurry was stirred for 10 minutes, then filtered. The solid was washed with MTBE (20 mL).

To the combined filtrates were added conc HCl (1,272 ml, 15.27 mmol, 1.2 eq). The resulting mixture was stirred overnight at room temperature and then concentrated to dryness. The residue was dissolved in propan-2-ol (20 mL) then concentrated to 2 vol (4 mL). To the resulting solution was then added MTBE (12 mL). a white crystalline solid crushed out. The slurry was stirred at room temperature for 1 h and then the solid was collected, washed with MTBE (4 mL), dried in a vacuum oven at 50° C. for 4 h. A first crop of white needles (884 mg) was obtained. the combined mother liquor and washes were concentrated to dryness. Isopropyl acetate (iPrOAc) was added to the residue, white crystals started to appear. More iPrOAc was added but some solids were crusted on the flask wall. Some DCM was added and clear solid was obtained. The DCM was removed and a white solid was crashed out, filtered and washed with iPrOAc. The white crystalline solid was dried in a vacuum oven at 50° C. for 4 h. A second crop of white needles (547 mg) was obtained. The N-methyl cyclopentylamine hydrochloride was obtained as white needles in 83% molar yield.

4.2 Reductive Amination Method

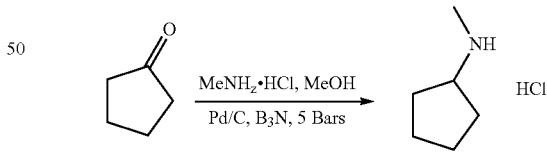

The use of cyclopentanone and N-methylamine hydrochloride in presence of a catalytic amount of triethylamine and Pd/C under hydrogen pressure in methanol at 65° C. was found to give the best results. Under these conditions, the N-methylcyclopentylamine hydrochloride was isolated as a white solid in 49% yield.

The source of palladium and reagent equivalents were tested to improve the yield and the quality of the product (removal of methylamine hydrochloride). Using Pd/C (JM, 5R39 paste) with a slight excess of Methyl amine hydrochloride (1.1 eq) it was possible to improve the yield up to 69%.

Note that the removal of methyl amine hydrochloride is feasible by suspending the N-methylcyclopentylamine hydrochloride in dichloromethane in the presence of sodium carbonate followed by distillation. No methylamine is detected in the final product.

Protocol Description

To palladium 5% on carbon, 5R 39 paste (0.75 g, 0.176 mmol, 0.001 eq) were added successively MeOH (105 ml), methylamine hydrochloride (13.24 g, 196 mmol), cyclopentanone (15.77 ml, 178 mmol) and finally triethylamine (0.621 ml, 4.46 mmol). The resulting slurry was placed into an autoclave and was charged with 5 bar hydrogen. The autoclave was heated at 65° C. and stirred overnight. The reaction mixture was cooled slowly and TLC (eluent PE/ethyl acetate 8:2, dip permanganate) showed no starting material. The black slurry was filtered through celite and washed with MeOH (10 mL). The methanol was removed and replaced by isopropanol (60 mL). The solution was concentrated to 2 vol and isopropyl ether (60 ml) was added. The resulting mixture was stirred at room temperature. A white solid was observed and then the slurry was stirred at 0° C. for 1 h, then filtered. The solid was washed with isopropyl ether/propan-2-ol 9:1 (30 mL), dried in a vacuum oven overnight. A white crystalline solid of N-methylcyclopentylamine HCl (16.9 g, 69.5% yield) was obtained.

The invention claimed is:

1. A compound having the following structure:

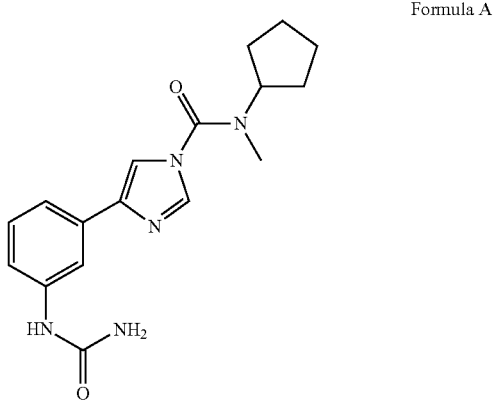 [SMILES: CN(C(=O)n1cnc(-c2cccc(NC(N)=O)c2)c1)C1CCCC1]

Formula A or a pharmaceutically acceptable salt thereof or a derivative in which the —NH—(C═O)—NH$_2$ group of Formula A is —NH—(C═O)—NHR or —NH—(C═O)—NR$_2$, wherein each R group is selected from C$_{1-18}$ alkyl, aryl, heteroaryl, and C$_{3-8}$ cycloalkyl.

2. A pharmaceutical composition comprising a compound according to claim 1, together with one or more pharmaceutically acceptable excipients.

3. The pharmaceutical composition of claim 2, further comprising one or more additional active pharmaceutical ingredients.

4. The pharmaceutical composition of claim 3, wherein the one or more additional active pharmaceutical ingredients is/are selected from the group consisting of anandamide, oleoyl ethanolamide, and palmitoyl ethanolamide.

5. A method of treatment of a condition whose development or symptoms are linked to a substrate of the FAAH enzyme, the method comprising the administration, to a subject in need of such treatment, of a therapeutically effective amount of a compound according to claim 1, wherein treatment is effected by increasing the levels of anandamide, N-oleoylethanolamine, N-palmitoylethanolamine, and/or oleamide, and wherein the condition is selected from appetite regulation, obesity, metabolic disorders, cachexia, anorexia, pain, inflammation, neurotoxicity, neurotrauma, stroke, multiple sclerosis, spinal cord injury, Parkinson's disease, levodopa-induced dyskinesia, Huntington's disease, Gilles de la Tourette's syndrome, tardive dyskinesia, dystonia, amyotrophic lateral sclerosis, Alzheimer's disease, epilepsy, schizophrenia, anxiety, depression, insomnia, nausea, emesis, alcohol disorders, drug addictions such as opiates, nicotine, cocaine, alcohol and psychostimulants, hypertension, circulatory shock, myocardial reperfusion injury, atherosclerosis, asthma, glaucoma, retinopathy, cancer, inflammatory bowel disease, acute and chronic liver disease such as hepatitis and liver cirrhosis, arthritis and osteoporosis.

* * * * *